United States Patent

Frank

[11] Patent Number: 5,585,550
[45] Date of Patent: Dec. 17, 1996

[54] DEVICE FOR DETECTING WATER IN FUEL

[76] Inventor: Sonya Frank, Rte. 3, Box 226A, Montgomery, Tex. 77356

[21] Appl. No.: 431,449

[22] Filed: May 1, 1995

[51] Int. Cl.⁶ .......................... B65B 1/30; G01N 33/18; C10G 33/04

[52] U.S. Cl. .......................... 73/61.43; 210/94; 141/94; 261/DIG. 40; 261/2; 208/177; 422/119

[58] Field of Search .................. 73/61.43, 61.44; 422/DIG. 42, 119; 210/94, 95; 208/177; 141/94, 96; 261/39, 40, 2

[56] References Cited

U.S. PATENT DOCUMENTS

| | | | |
|---|---|---|---|
| 895,083 | 8/1908 | Gardiner | 261/DIG. 40 |
| 2,761,312 | 9/1956 | Line et al. | 73/53 |
| 2,844,025 | 7/1958 | Joyce et al. | 73/53 |
| 3,106,836 | 10/1963 | Nesh | 73/53 |
| 3,219,071 | 11/1965 | Ferster | 141/94 |
| 3,499,316 | 3/1970 | Krause | 73/61.1 |
| 3,964,295 | 6/1976 | Stenstrom | 73/61.1 R |
| 3,971,248 | 7/1976 | Christensen | 73/61.1 R |
| 4,004,453 | 1/1977 | Thyrum | 73/61.43 |
| 4,227,818 | 10/1980 | Gacki et al. | 366/142 |
| 4,396,498 | 8/1983 | Dente et al. | 208/188 |
| 4,469,149 | 9/1984 | Walkey et al. | 141/94 |
| 4,993,460 | 2/1991 | Robinson et al. | 141/94 |
| 5,244,017 | 9/1993 | Hartman et al. | 141/5 |
| 5,316,057 | 5/1994 | Hasselmann | 141/94 |
| 5,349,994 | 9/1994 | Koeninger | 141/94 |

*Primary Examiner*—Hezron E. Williams
*Assistant Examiner*—J. David Wiggins
*Attorney, Agent, or Firm*—Kenneth A. Roddy

[57] ABSTRACT

A device adapted to be placed between a fuel storage tank and a fuel container into which the fuel is to be pumped, for example on a fuel pump nozzle, for detecting the presence of water in the fuel being pumped. The device has a tubular member with an inlet for receiving a portion of the fuel being pumped, an outlet for discharging the portion of fuel conducted through the tubular member, and a transparent portion disposed between the inlet and outlet. A chemical paste composition containing a water responsive indicator dye is disposed in the transparent portion of the tubular member to contact the portion of fuel conducted through the tubular member and produces a visually noticeable color change indicating the presence of water in the fuel being pumped.

21 Claims, 3 Drawing Sheets

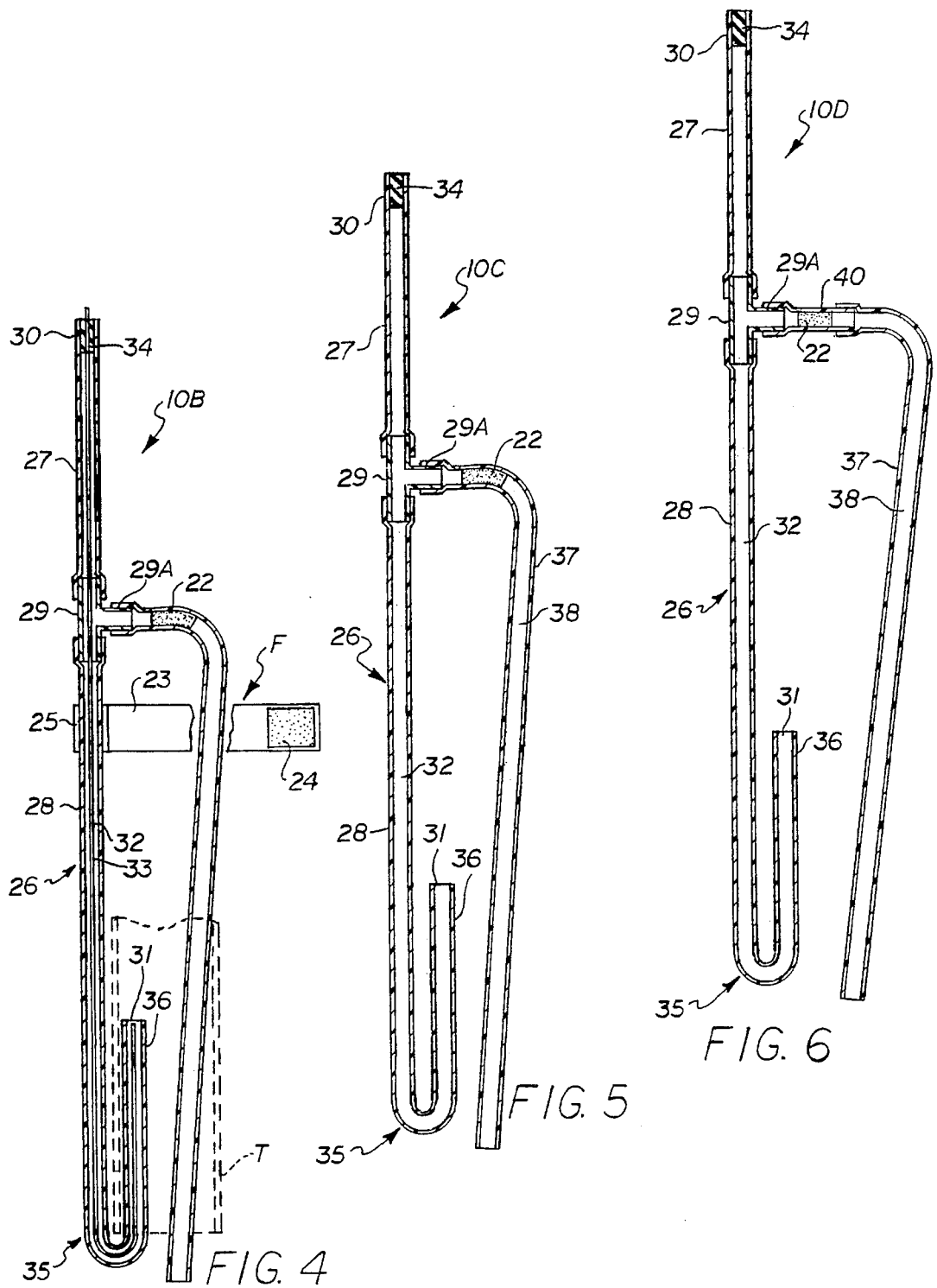

DEVICE FOR DETECTING WATER IN FUEL

BACKGROUND OF THE INVENTION

1. Field of the Invention

This invention relates generally to apparatus for detecting water in fuel, and more particularly to a device which is connected to a fuel nozzle or gas tank and has a transparent tubular portion with a color change chemical paste composition disposed therein to visually detect the presence of water in the fuel being pumped.

2. Brief Description of the Prior Art

Fuel storage tanks at gas service stations are subject to being diluted by water. A motorist has no way of knowing the quality of the fuel being pumped into their vehicle until they begin to have problems with the engine. The water diluted fuel may cause knocking and pinging or stalling of the engine, and in some instances may damage the carburetor, fuel pump, fuel injectors, fuel system and internal engine components, resulting in costly repairs. If water is detected in the fuel, the gas tank must be drained.

There are several patents which disclose various devices for detecting contaminated fuel.

Gray et al, U.S. Pat. No. 4,517,547 discloses a sensing circuit connected with a probe capacitor positioned within a fuel tank which detects excessive water in the fuel of a vehicle. As the water content increases, the capacitance of the variable capacitor probe increases thereby reducing the magnitude of a rectified current. As the magnitude of the rectified current decreases below the magnitude of a known current, the sensing circuit produces a signal to turn on a warning light on the dash of the vehicle.

Sutton, U.S. Pat. No. 4,638,305 discloses an electrically conductive metal probe or siphon tube coupled to an electronic detection circuit which detects the presence of water in diesel or other fuel oil. The electrical circuit is responsive to either low resistance or high capacitance between the probe and ground. The probe makes a resistive coupling to the fuel container when accumulated water touches the probe. When insulating deposits from the fuel coat the probe, capacitive coupling will occur between the probe and accumulated water.

It is known in the art to coat the lower end of a gasoline storage tank measuring stick or gauge with a color change chemical paste composition. The gauge is lowered into the storage tank and then removed. The lower portion of the coated gauge will change color to show the depth of a water/fuel mixture.

Chemical paste compositions which change color in the presence of water are known in the art. The present invention, in a preferred embodiment, utilizes a commercially available color change chemical paste composition, but does not attempt to claim a color change chemical paste composition per se. One example of a commercially available color change chemical paste suitable for use is sold by Kolor Kut Products, Inc., of Houston, Tex. under the trademark "KOLOR KUT"™.

Melpolder et al, U.S. Pat. No. 4,699,885, and Melpolder, U.S. Pat. Nos. 4,578,357 and 4,717,671, hereby incorporated by reference, also disclose suitable color change chemical paste compositions.

These types of color change chemical paste compositions are used to coat the lower end of a gasoline storage tank measuring stick or gauge which is used to test the fuel stored in the storage tank. The gauge is lowered into the storage tank and then removed. The lower portion of the coated gauge will change color to show the depth of a water/fuel mixture. In some cases, the stored fuel is not tested, or only occasionally tested, and the motorist has no way of knowing whether the fuel he or she is putting into the vehicle has been tested.

The present invention is distinguished over the prior art in general, and these patents in particular by a device adapted to be placed between a fuel storage tank and a fuel container into which the fuel is to be pumped, for example on a fuel pump nozzle, for detecting the presence of water in the fuel being pumped. The device has a tubular member with an inlet for receiving a portion of the fuel being pumped, an outlet for discharging the portion of fuel conducted through the tubular member, and a transparent portion disposed between the inlet and outlet. A chemical paste composition containing a water responsive indicator dye is disposed in the transparent portion of the tubular member to contact the portion of fuel conducted through the tubular member and produces a visually noticeable color change indicating the presence of water in the fuel being pumped.

SUMMARY OF THE INVENTION

It is therefore an object of the present invention to provide a device for detecting the presence of water in fuel.

It is another object of this invention to provide a device for detecting the presence of water in fuel which is easily and quickly connected to a fuel nozzle prior to pumping fuel into a vehicle gas to detect the presence of water in the fuel being pumped and thereafter easily and quickly removed.

Another object of this invention is to provide a device for detecting the presence of water in fuel which is connected to the neck of a vehicle gas tank to detect the presence of water in the fuel being pumped thru it into the vehicle gas tank.

Another object of this invention is to provide a device for visually detecting the presence of water in fuel which does not require electronic circuitry.

Another object of this invention is to provide a device for visually detecting the presence of water in fuel which effects a color change upon direct contact with water.

Another object of this invention is to provide a small, compact device for visually detecting the presence of water in fuel which device may be stored in a small space readily available for use when filling the fuel tank of a vehicle.

A further object of this invention is to provide a device on the neck of a fuel tank for visually detecting the presence of water in fuel which is being pumped into the fuel tank.

A still further object of this invention is to provide a device for detecting the presence of water in fuel which is simple in construction and economical to manufacture.

Other objects of the invention will become apparent from time to time throughout the specification and claims as hereinafter related.

The above noted objects and other objects of the invention are accomplished by a device adapted to be placed between a fuel storage tank and a fuel container into which the fuel is to be pumped, for example on a fuel pump nozzle, for detecting the presence of water in the fuel being pumped. The device has a tubular member with an inlet for receiving a portion of the fuel being pumped, an outlet for discharging the portion of fuel conducted through the tubular member, and a transparent portion disposed between the inlet and outlet. A chemical paste composition containing a water responsive indicator dye is disposed in the transparent portion of the tubular member to contact the portion of fuel conducted through the tubular member and produces a visually noticeable color change indicating the presence of water in the fuel being pumped.

BRIEF DESCRIPTION OF THE DRAWINGS

FIG. 4 is a longitudinal cross section through an alternate embodiment of the bendable device for detecting the presence of water in a fuel.

FIG. 5 is a longitudinal cross section through an alternate embodiment of the rigid device for detecting the presence of water in a fuel.

FIG. 6 is a longitudinal cross section through an embodiment of the device for detecting the presence of water in a fuel which has a replaceable cartridge containing a color change chemical paste composition.

DESCRIPTION OF THE PREFERRED EMBODIMENTS

Figure 1:
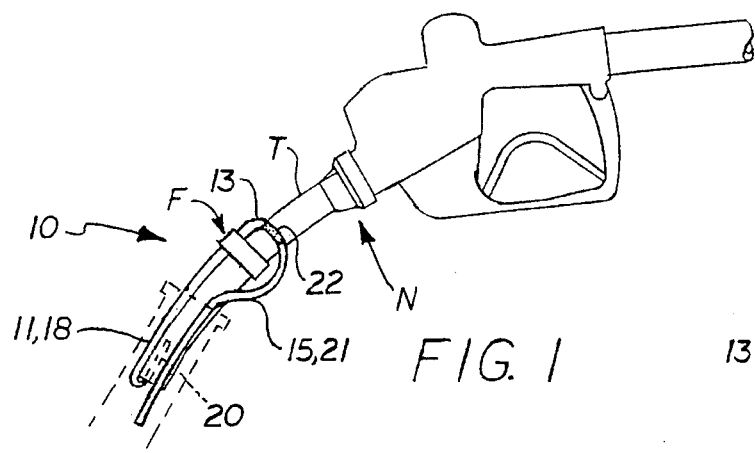
FIG. 1 is a side elevation of a device for detecting the presence of water in a fuel in accordance with the present invention shown attached to a fuel nozzle.

Referring to the drawings by numerals of reference, there is shown in FIG. 1, a device 10 for detecting the presence of water in a fuel in accordance with one preferred embodiment of the invention shown attached to a conventional fuel nozzle N of the type used in most service stations.

Figure 2:
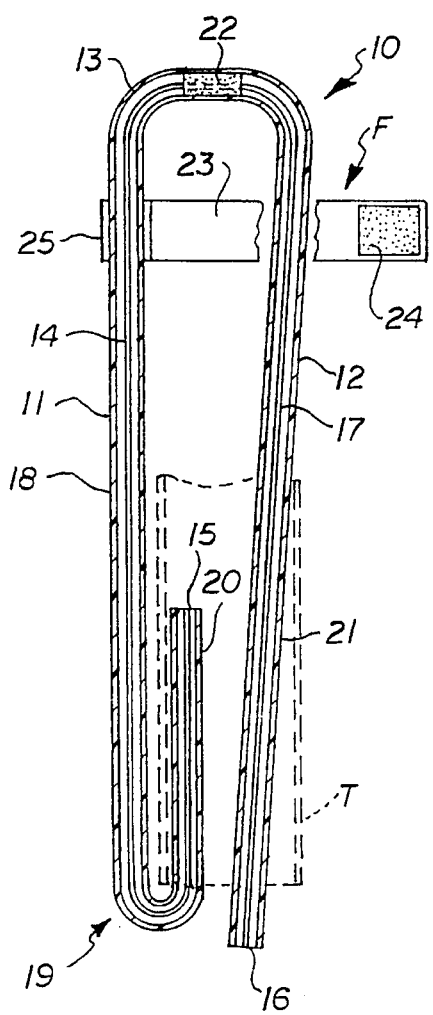
FIG. 2 is a longitudinal cross section through a bendable embodiment of the device for detecting the presence of water in a fuel.

FIG. 2 shows an embodiment the device 10 that is formed of pliable tubing which may be bent to fit onto the outlet tube T of the fuel nozzle N. The device 10 is a generally inverted U-shaped member formed of small diameter transparent tubing having a first elongate leg 11 and a second elongate leg 12 with a curved portion 13 therebetween. A central passageway 14 extends between an inlet end 15 and an outlet end 16. A length of bendable wire 17 contained within the central passageway 14 extends from end to end. The first elongate leg 11 of the device 10 serves as a fuel inlet portion 18. The lower end of the fuel inlet portion 18 and wire 17 is bent upwardly to form a generally J-shaped configuration 19, the shorter leg 20 of which extends upwardly a short distance to be received inside the open end of the outlet tube T of a conventional fuel nozzle. The bent J-shaped portion and curved portion of the device retain the wire within the central passageway 14. The second elongate leg 12 of the device 10 serves as the fuel return portion 21 and extends into the filler neck of the vehicle gas tank.

A chemical paste composition 22 containing an indicator dye capable of producing a detectable color change responsive to contact by water is contained in the central passageway 14 of the device 10 to indicate the presence of water in the fuel passing through the return tube. Because the device is transparent, it can be also be visually determined whether or not fuel is being pumped into the fuel tank. The color change chemical composition 22 is responsive to water but is not responsive to hydrocarbons.

Suitable color change chemical paste compositions are commercially available. One example of a commercially available color change chemical paste suitable for use is sold by Kolor Kut Products, Inc., of Houston, Texas under the trademark "KOLOR KUT"™. U.S. Pat. Nos. 4,699,885, 4,578,357, and 4,717,671, to Melpolder and others, hereby incorporated by reference, also disclose suitable color change chemical paste compositions.

In the embodiment of FIG. 2, the color change chemical paste composition 22 may be applied to the interior passageway 14 of the device 10 by inserting a suitable tool into one open end and injecting the paste.

A fastener F may also be provided for securing the device 10 to a conventional fuel nozzle. A flexible strip 23 having mating elements of hook and loop fastener material 24 at opposite ends or on opposite sides may be secured to the tubular fuel inlet portion 18 by a loop of material 25. The strip 23 is wrapped around the fuel nozzle tube T and the mating elements of the fastener material are engaged to secure the device to the nozzle, as shown in FIG. 1. It should be understood that other types of conventional fasteners may be used, such as a clip or clamp arrangement.

Figure 3:
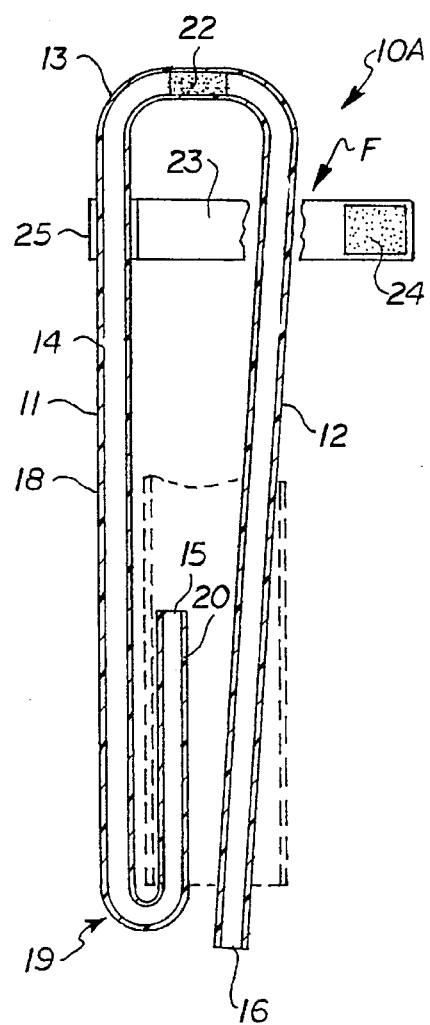
FIG. 3 is a longitudinal cross section through a rigid embodiment of the device for detecting the presence of water in a fuel.

FIG. 3 shows an alternate embodiment given by the device 10A that is formed of rigid tubing and is preshaped to fit into the outlet tube T of the fuel nozzle N. In this embodiment, no wire is required. The device 10A is a generally inverted U-shaped member formed of small diameter transparent tubing having a first elongate leg 11, a second elongate leg 12, a curved portion 13 therebetween, and a central passageway 14 extending between the inlet end 15 and outlet end 16. As previously described, the first elongate leg 11 of the device serves as a fuel inlet portion 18 and has a lower end which is bent upwardly to form a generally J-shaped configuration 19, the shorter leg 20 of which extends upwardly a short distance to be received inside the open end of the outlet tube T of a conventional fuel nozzle. Also, as previously described, a chemical paste composition 22 containing an indicator dye capable of producing a detectable color change responsive to contact by water is contained in the central passageway 14. As previously shown and described with reference to FIG. 2, but not repeated here, a fastener F may also be provided for securing the device 10A to a conventional fuel pump nozzle.

FIG. 4 shows another embodiment given by the bendable device 10B which is formed of pliable tubing that may be bent to conform to the shape of the outlet tube T of the fuel nozzle N. The device 10B has an elongate tubular fuel inlet portion 26 formed of an upper section 27 and lower section 28 of tubing joined together by a tee 29. The fuel inlet portion 26 has a top and bottom end 30 and 31, respectively and a central passageway 32 extending therebetween. A length of bendable wire 33 contained within the central passageway 32 extends through the tee 29 and is secured at its top end in a sealing plug 34 which forms a fluid seal at the top end of the passageway 32 and its bottom end terminates at the open bottom end 31 of the fuel inlet portion 26. The lower portion of the fuel inlet portion 26 and wire 33 is bent upwardly to form a generally J-shaped configuration 35, the shorter leg 36 of which extends upwardly a short distance into the open end of the outlet tube T of a conventional fuel pump nozzle.

The previously described fastener F may also be provided for securing the device 10B to a conventional fuel nozzle. The fastener components were described with reference to FIG. 2, and the same reference numerals are shown but the detailed description of the fastener is not repeated. It should be understood that other types of conventional fasteners may be used, such as a clip or clamp arrangement.

An elongate fuel return tube 37 formed of transparent flexible tubular material is releasably connected to the outlet 29A of the tee 29 and has a central passageway 38. A chemical paste composition 22, as described above, containing an indicator dye capable of producing a detectable color change responsive to contact by water is contained in the central passageway 38 of the return tube 37 to indicate the presence of water in the fuel passing through the return tube.

In the embodiment of FIG. 4, the color change chemical paste composition 22 may be applied to the interior passageway 25 of the return tube 37 by dipping one end of the return tube into a container of the paste and then installing that end of the return tube onto the outlet 29A of the tee 29. This may be done repeatedly as needed.

FIG. 5 shows another embodiment the device 10C that is formed of rigid tubing which is preformed to fit onto the outlet tube T of the fuel nozzle N. As described above with reference to FIG. 4, the device 10C has an elongate tubular fuel inlet portion 26 formed of an upper section 27 and lower section 28 of rigid tubing joined together by a tee 29. The fuel inlet portion 26 has a top and bottom end 30 and 31, respectively and a central passageway 32 extending therebetween. The passageway 32 is sealed at its top end by a sealing plug 34 which forms a fluid seal and the passageway terminates at the open bottom end 31 of the fuel inlet portion 26. The lower portion of the fuel inlet portion 26 is shaped to form a generally J-shaped configuration 35, the shorter leg 36 of which extends upwardly a short distance into the open end of the outlet tube of a conventional fuel pump nozzle, as shown in FIGS. 1–4. The device 10C may also be provided with a fastener, as described above, for securing it to a conventional pump fuel nozzle.

An elongate fuel return tube 37 formed of transparent material which may be either flexible or rigid is releasably connected to the outlet 29A of the tee 29 and has a central passageway 38. A chemical paste composition 22, as previously described, containing an indicator dye capable of producing a detectable color change responsive to contact by water is contained in the central passageway 38 of the return tube 37 to indicate the presence of water in the fuel passing through the return tube. The color change chemical paste composition 22 may be applied to the interior passageway 38 of the return tube 37 by dipping one end of the return tube into a container of the paste and then installing that end of the return tube onto the outlet 29A of the tee 29, as previously described.

FIG. 6 shows an embodiment of the device 10D for detecting the presence of water in a fuel which has a replaceable transparent cartridge 40 containing a color change chemical paste composition 26, wherein the cartridges may be removed and replaced as needed. The embodiment of FIG. 6 has the same structure, as previously described, and the reference numerals are shown in the drawing figure, but will not be described again in detail to avoid repetition. In the embodiment of FIG. 6, the color change chemical paste composition 22 is contained within a tubular cartridge 40 formed of transparent material. The cartridge 40 is adapted at one end to be connected with the outlet 29A of the tee 29, and its opposite end is adapted to be connected with the return tube 37. In this embodiment, only the cartridge needs to be transparent, and the remaining tubular components may be opaque. It should be understood that the cartridge may be used with either the rigid embodiment of FIG. 5 or the flexible embodiment of FIG. 4. It should also be understood that the device may be made of a combination of flexible and tubular members.

As shown in FIGS. 1 and 2, the device 10 is installed by inserting the upwardly bent portion 20 of the fuel inlet portion 18 into the open bottom end of the tube T of the fuel pump nozzle N and securing the upper portion of the device to the exterior of the nozzle tube by the fastener F such that the transparent return portion 21 (or transparent cartridge 40) is visible, inserting the lower portion of the return leg 21 alongside the exterior of the nozzle tube, and then inserting the nozzle tube into the neck of the fuel tank in the usual manner. As fuel is pumped into the tank, a portion of the fuel is directed upwardly into the fuel inlet portion 18 and through the curved portion 13 (or transparent cartridge 40) into the return portion 21.

A few seconds after the fuel contacts the color change chemical paste composition 22 it will dissolve or wash away a portion of the paste and flow through the return line to the fuel tank. Any water present in the fuel as it contacts and passes through paste will be detected by the water sensitive dye component of the paste and produce a noticeable color change in the paste. If the color change appears, the pump may be stopped before the tank is appreciably filled with the water contaminated fuel.

Figure 7:
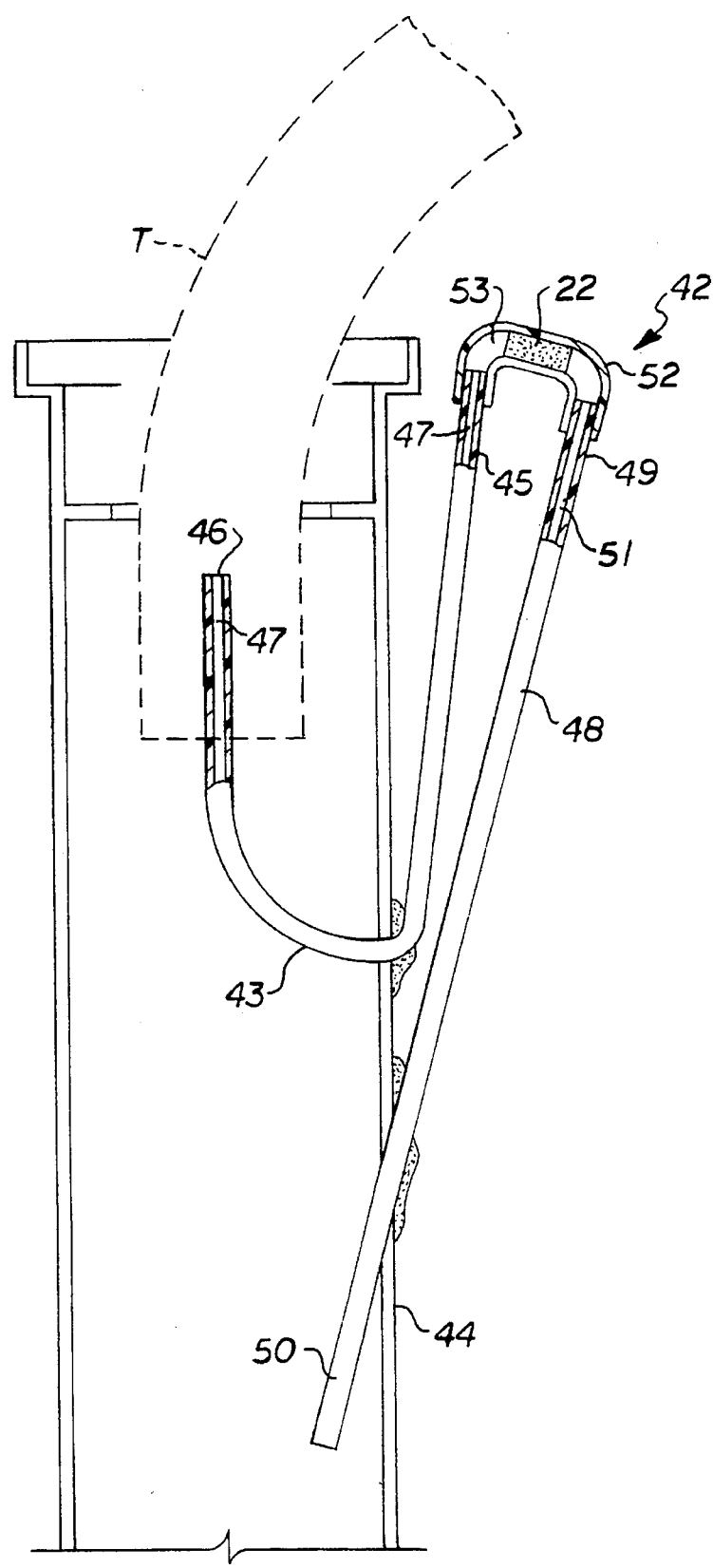
FIG. 7 is a longitudinal cross section through the neck of a vehicle fuel tank which is modified to have a device for detecting the presence of water in accordance with the present invention.

FIG. 7 shows the neck 41 of a vehicle fuel tank which is modified to have a device 42 for detecting the presence of water in a fuel when filling the tank. An elongate tubular fuel inlet tube 43 formed of rigid tubing extends from the exterior of the neck 41, through its side wall 44, and into the interior of the neck. The inlet tube 43 is secured to the neck 41 by welding or other suitable means to form a fluid tight seal therebetween. The fuel inlet tube 43 has a top end 45 exterior of the neck 41, a bottom end 46 disposed in the interior of the neck, and a central passageway 47 extending from end to end. The lower portion of the fuel inlet tube 43 inside the neck 41 is bent upwardly to form a generally J-shaped configuration which extends upwardly a short distance toward the open end of the neck to position the open bottom end 46 of the fuel inlet tube such that it will be received in the open end of the outlet tube T of a conventional fuel nozzle N when it is inserted into the neck of the fuel tank when filling the vehicle. The upper portion of the fuel inlet tube 43 extends upwardly from the exterior of the neck 41 a sufficient distance such that its top end 45 can seen by a person filling the fuel tank.

An elongate tubular fuel return tube 48 formed of rigid tubing extends from the exterior of the neck 41, through its side wall 44, and into the interior of the neck. The return tube 48 is secured to the neck 41 by welding or other suitable means to form a fluid tight seal therebetween. The fuel return tube 48 has a top end 49 exterior of the neck 41, a bottom end 50 disposed in the interior of the neck, and a central passageway 51 extending from end to end. The bottom end 50 of the fuel return tube 48 is disposed below the fuel inlet tube 43 and faces downward to direct fuel flowing through the central passageway 51 into the fuel tank below. The upper portion of the fuel inlet tube 48 extends upwardly from the exterior of the neck 41 a sufficient distance to position its top end 49 adjacent the top end 45 of the fuel inlet tube 43.

A short transparent tubular member 52 having a central passageway 53 is releasably connected at opposite ends between the top end 45 of the fuel inlet tube 43 and the top end 49 of the fuel return tube 48. A chemical paste composition 22 containing an indicator dye capable of producing a detectable color change responsive to contact by water is contained in the central passageway 53 of the transparent tubular member 52 to indicate the presence of water in the fuel passing therethrough.

The transparent tubular member 52 may be formed of rigid or flexible tubing, and the color change chemical paste composition 22 may be applied to its passageway 53 by dipping one end of the return tube into a container of the paste and then installing both of its ends onto the top ends 45 and 49 of the fuel inlet and return tubes 43 and 48, respectively.

Alternatively, the transparent tubular member 52 may be provided in the form of a replaceable transparent cartridge containing the color change chemical paste composition, wherein the cartridges may be removed and replaced as needed.

While this invention has been described fully and completely with special emphasis upon several preferred embodiments, it should be understood that within the scope of the appended claims the invention may be practiced otherwise than as specifically described herein.

I claim:

1. A sensor device for detecting the presence of water in fuel being pumped from a fuel storage tank by means of a fuel transfer line with a fuel transfer element attached at the end thereof, comprising:

a tubular member adapted to be placed on a fuel transfer element disposed between a fuel storage tank and a fuel container into which a fuel is to be pumped, said tubular member having an inlet for receiving a portion of the fuel being pumped from said fuel transfer element, an outlet for discharging the portion of fuel conducted through said tubular member, and a transparent portion disposed between said inlet and said outlet; and water responsive visual indicating means disposed in said transparent portion of said tubular member to contact said portion of fuel conducted through said tubular member and produce a visual signal responsive to contact by water to indicate the presence of water in said portion of fuel passing through said tubular member while said portion of fuel is discharged from said device thru said outlet.

2. The device according to claim 1 in which said visual indicating means comprises a chemical paste composition containing an indicator dye capable of producing a detectable color change responsive to contact by water to indicate the presence of water in the fuel passing through said tubular member.

3. The device according to claim 1 in which said tubular member transparent portion is a transparent cartridge containing said water responsive visual indicating means.

4. The device according to claim 1 in which said tubular member is secured to a fuel pump nozzle connected with the fuel storage tank from which the fuel is being pumped;

said tubular member inlet is positioned to receive a portion of the fuel being pumped; and said tubular member outlet is positioned to discharge the portion of fuel conducted through said tubular member into the fuel container into which the fuel is being pumped by the nozzle after contact with said visual indicating means.

5. The device according to claim 1 in which said tubular member is releasably connected to a fuel pump nozzle connected with the fuel storage tank from which the fuel is being pumped;

said tubular member inlet is positioned in the open bottom end of the nozzle for receiving a portion of the fuel being pumped; and said tubular member outlet is positioned to discharge the portion of fuel conducted through said tubular member into the fuel container into which the fuel is being pumped by the nozzle after contact with said visual indicating means.

6. The device according to claim 5 further comprising fastener means for releasably connecting said tubular member to said nozzle.

7. The device according to claim 5 in which said tubular member is pliable and capable of being manually shaped to position said tubular member inlet in the open bottom end of the nozzle for receiving a portion of the fuel being pumped and to position said tubular member outlet to conduct the discharged portion of fuel conducted through said tubular member into the fuel container into which the fuel is being pumped.

8. The device according to claim 7 in which said tubular member comprises a flexible tubular member; and a pliable wire contained within said pliable tubular member capable of being bent and thereafter retaining the shape into which it is bent.

9. The device according to claim 1 in which said tubular member has a generally J-shaped lower portion with the shorter upwardly directed portion defining said tubular member inlet and positioned in the open bottom end of the nozzle for receiving a portion of the fuel being pumped, and the longer upwardly directed portion having a laterally extending outlet; and a tubular fuel return tube connected at an upper end with said laterally extending outlet and having a lower end defining said tubular member outlet and positioned to discharge the portion of fuel conducted through said tubular member into the fuel container into which the fuel is being pumped by the nozzle after contact with said visual indicating means.

10. The device according to claim 9 in which at least a portion of said tubular fuel return tube is transparent; and said water responsive visual indicating means is contained within said transparent portion of said fuel return tube.

11. The device according to claim 9 including a transparent tubular cartridge containing said water responsive visual indicating means;

said cartridge having a first end removably connected with said laterally extending outlet and a second end adapted to receive said fuel return tube; and said tubular fuel return tube is releasably connected with said second end of said cartridge.

12. The device according to claim 1 in which said tubular member is secured to a filler neck of a vehicle fuel tank which receives a fuel pump nozzle connected with the fuel storage tank from which the fuel is being pumped;

said tubular member inlet is positioned to receive a portion of the fuel being pumped into the vehicle fuel tank; and said tubular member outlet is positioned to discharge the portion of fuel conducted through said tubular member into the vehicle fuel tank after contact with said visual indicating means.

13. The device according to claim 12 in which said tubular member has a generally J-shaped lower portion with the shorter upwardly directed portion disposed within the filler neck and defining said tubular member inlet and positioned to receive the open bottom end of the nozzle for receiving a portion of the fuel being pumped, and the longer upwardly directed portion extending outwardly from said neck; and a tubular fuel return tube having an upper end exterior of the filler neck connected at an upper end with said longer upwardly directed portion and having a lower end disposed within the filler neck defining said tubular member outlet and positioned to discharge the portion of fuel conducted through said tubular member into the vehicle fuel tank after contact with said visual indicating means.

14. The device according to claim 13 in which at least a portion of said tubular fuel return tube is transparent; and said water responsive visual indicating means is contained within said transparent portion of said fuel return tube.

15. The device according to claim 13 including a transparent tubular cartridge containing said water responsive visual indicating means;

said cartridge having one end removably connected with said longer upwardly directed portion extending outwardly from said neck, and another end adapted to receive said fuel return tube; and said tubular fuel return tube is releasably connected with said another end of said cartridge.

16. The combination of a fuel pump nozzle and a sensor device for detecting the presence of water in fuel being pumped through the nozzle from a fuel storage tank comprising:

a fuel pump nozzle connected with a fuel storage tank for pumping fuel from the fuel storage tank into a fuel container;

where said device comprises a tubular member on said fuel pump nozzle having an inlet which receives a portion of the fuel being pumped, an outlet which discharges the portion of fuel conducted through said tubular member, and a transparent portion disposed between said inlet and said outlet; and water responsive visual indicating means disposed in said transparent portion of said tubular member to contact said portion of fuel conducted through said tubular member and produce a visual signal responsive to contact by water to indicate the presence of water in said portion of fuel passing through said tubular member while said portion of fuel is discharged from said device thru said outlet and into said fuel container.

17. The combination according to claim 16 in which said visual indicating means comprises a chemical paste composition containing an indicator dye capable of producing a detectable color change responsive to contact by water to indicate the presence of water in the fuel passing through said tubular member.

18. The combination according to claim 16 in which said tubular member transparent portion is a transparent cartridge containing said water responsive visual indicating means.

19. The combination of a filler neck of a vehicle fuel tank and a sensor device for detecting the presence of water in fuel being pumped into the fuel tank through the filler neck via a fuel pump nozzle inserted into said filler neck comprising;

a filler neck connected with a vehicle fuel tank to receive the outlet end of a fuel pump nozzle connected with a fuel storage tank from which fuel is pumped;

a tubular member on said filler neck having an inlet positioned relative to said outlet end of said pump nozzle to receive a portion of the fuel being pumped into the fuel tank, an outlet which discharges the portion of fuel conducted through said tubular member back into said filler neck, and a transparent portion disposed between said inlet and said outlet; and water responsive visual indicating means disposed in said transparent portion of said tubular member to contact said portion of fuel conducted through said tubular member and produce a visual signal responsive to contact by water to indicate the presence of water in said portion of fuel passing through said tubular member while said portion of fuel is discharged from said device thru said outlet and into said fuel tank.

20. The combination according to claim 19 in which said visual indicating means comprises a chemical paste composition containing an indicator dye capable of producing a detectable color change responsive to contact by water to indicate the presence of water in the fuel passing through said tubular member.

21. The combination according to claim 19 in which said tubular member transparent portion is a transparent cartridge containing said water responsive visual indicating means.

\* \* \* \* \*